United States Patent
Nguyen et al.

(10) Patent No.: US 11,247,962 B2
(45) Date of Patent: Feb. 15, 2022

(54) METHODS OF CHEMICAL RECOVERY FOR PROPYLENE OXIDE-STYRENE MONOMER PROCESSES

(71) Applicant: Lyondell Chemical Technology, L.P., Houston, TX (US)

(72) Inventors: Ha H. Nguyen, Houston, TX (US); Anthony S. Dearth, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 42 days.

(21) Appl. No.: 16/868,091

(22) Filed: May 6, 2020

(65) Prior Publication Data
US 2020/0354300 A1 Nov. 12, 2020

Related U.S. Application Data

(60) Provisional application No. 62/844,539, filed on May 7, 2019.

(51) Int. Cl.
| | | |
|---|---|---|
| *C07C 45/82* | (2006.01) | |
| *B01D 3/00* | (2006.01) | |
| *C07C 45/83* | (2006.01) | |
| *B01D 3/14* | (2006.01) | |
| *B01D 11/04* | (2006.01) | |
| *B01D 15/08* | (2006.01) | |
| *C07C 29/84* | (2006.01) | |

(52) U.S. Cl.
CPC .............. *C07C 45/83* (2013.01); *B01D 3/143* (2013.01); *B01D 11/0446* (2013.01); *B01D 11/0488* (2013.01); *B01D 15/08* (2013.01); *C07C 29/84* (2013.01)

(58) Field of Classification Search
CPC .......... C07C 45/83; C07C 29/84; B01D 3/143
See application file for complete search history.

(56) References Cited

U.S. PATENT DOCUMENTS

| | | | |
|---|---|---|---|
| 3,351,635 A | 11/1967 | Chong | |
| 5,210,354 A | 5/1993 | Dubner et al. | |
| 5,273,235 A | 12/1993 | Sato | |
| 10,526,549 B2 * | 1/2020 | Nagy | ................... B01J 27/0515 |
| 2010/0078391 A1 | 4/2010 | Lindsey et al. | |
| 2018/0221787 A1 | 8/2018 | Nagy et al. | |
| 2018/0312764 A1 | 11/2018 | Nagy et al. | |

OTHER PUBLICATIONS

The International Search Report and The Written Opinion for PCT/US2020/031646 dated Aug. 25, 2020.

* cited by examiner

Primary Examiner — Sikarl A Witherspoon

(57) ABSTRACT

Methods and systems for recovering materials from streams from processes for the co-production of propylene oxide and styrene monomer. The processes may permit the recovery of products, such a mono-propylene glycol, or the recycling of products, such as α-methyl benzyl alcohol.

22 Claims, 5 Drawing Sheets

METHODS OF CHEMICAL RECOVERY FOR PROPYLENE OXIDE-STYRENE MONOMER PROCESSES

CROSS-REFERENCE TO RELATED APPLICATION

This application claims the benefit of priority to U.S. Provisional Application No. 62/844,539 filed May 7, 2019, which is incorporated here by reference in its entirety.

FIELD OF THE INVENTION

This disclosure generally relates to methods and systems for recovering one or more chemicals from one or more streams created by processes for the co-production of propylene oxide and styrene monomer.

BACKGROUND

Methods of co-producing propylene oxide and styrene monomer ("POSM" processes) include the oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol (also known as α-methyl benzyl alcohol) to produce styrene monomer. An example of a POSM process is described at U.S. Pat. No. 3,351,635. POSM processes also are described at U.S. Pat. Nos. 5,210,354 and 5,276,235, and U.S. Patent Application Publication No. 2018/0221787, which disclose methods for upgrading a low value heavy residue produced during the processes. Each of these references are incorporated herein by reference.

In POSM processes there may be multiple purge streams that contain one or more recoverable chemicals, including, but not limited to, mono propylene glycol, α-methyl benzyl alcohol, benzaldehyde, and/or acetophenone. These purge streams may be treated as waste streams, and, in some instances, used as fuel.

There remains a need for methods and systems that are capable of recovering one or more chemicals from one or more streams created by POSM processing, including, but not limited to, one or more chemicals that can be recycled into a POSM process, used as a fuel, purified to obtain a final commercial product and/or a product that may be used in a different process, or a combination thereof.

BRIEF SUMMARY

Provided herein are methods that address one or more of the foregoing needs, including methods that permit the recovery of one or more chemicals from streams, including purge streams, drawn from processes for co-producing propylene oxide and styrene monomers. One or more of the recovered chemicals may be recycled in a process, such as a POSM process.

In some embodiments, the methods provided herein include providing at least one stream from a process for co-producing propylene oxide and styrene monomer; disposing the at least one stream in a settling tank to separate the at least one stream into an aqueous stream and an organic stream, wherein the aqueous stream includes (i) mono-propylene glycol, and (ii) a first amount of α-methyl benzyl alcohol (also known as 1-phenyl ethanol), a first amount of benzaldehyde, a first amount of acetophenone, or a combination thereof; and contacting the aqueous stream with an organic extraction liquid in a liquid-liquid extraction unit to form a first aqueous extraction stream and a first organic extraction stream; wherein the first aqueous extraction stream includes (i) mono-propylene glycol, and (ii) a second amount of α-methyl benzyl alcohol, a second amount of benzaldehyde, a second amount of acetophenone, or a combination thereof, and the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

In some embodiments, the methods also include contacting the first aqueous extraction stream with an additional amount of the organic extraction liquid to form a second aqueous extraction stream and a second organic extraction stream; wherein the second aqueous extraction stream includes (i) mono-propylene glycol, and (ii) a third amount of α-methyl benzyl alcohol, a third amount of benzaldehyde, a third amount of acetophenone, or a combination thereof, and the third amount of α-methyl benzyl alcohol, the third amount of benzaldehyde, and the third amount of acetophenone are less than the second amount of α-methyl benzyl alcohol, the second amount of benzaldehyde, and the second amount of acetophenone, respectively.

In some embodiments, the methods also include separating mono-propylene glycol, benzaldehyde, α-methyl benzyl alcohol, acetophenone, or a combination thereof from a first aqueous extraction stream, a first organic extraction stream, or a combination thereof.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION OF THE INVENTION

Figure 1:
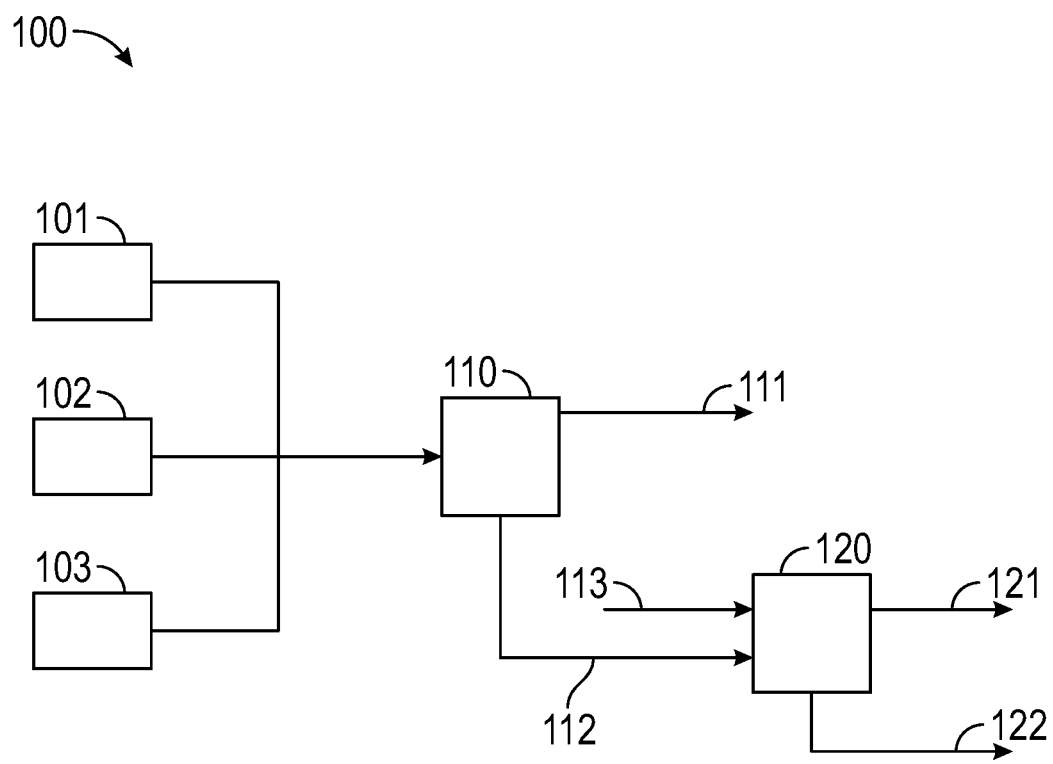
FIG. 1 depicts a schematic of an embodiment of a system for performing embodiments of the methods described herein.

Methods are provided for recovering one or more chemicals from one or more streams drawn from a process for co-producing propylene oxide and styrene monomer. In some embodiments, the methods provided herein include providing at least one stream from a process for co-producing propylene oxide and styrene monomer; disposing the at least one stream in a settling tank to separate the at least one stream into an aqueous stream and an organic stream.

In some embodiments, one stream from a process for co-producing propylene oxide and styrene monomer is disposed in the settling tank. In some embodiments, two streams from a process for co-producing propylene oxide and styrene monomer are disposed in the settling tank. In some embodiments, three streams from a process for co-producing propylene oxide and styrene monomer are disposed in the settling tank. In some embodiments, more than three streams (e.g., 4 to 10 streams) from a process for co-producing propylene oxide and styrene monomer are disposed in the settling tank. When more than one stream is disposed in a settling tank, one or more of the streams may be directly disposed in the settling tank, one or more of the streams may be combined prior to being disposed in the settling tank, or a combination thereof. In some embodiments, the at least one stream from the process for preparing propylene oxide and styrene monomer includes a purge stream.

The settling tank may include any known settling tank. The settling tank generally may include a reservoir, at least one inlet, and at least one outlet. In some embodiments, the weight ratio of the organic stream to the aqueous stream in the settling tank is about 50-75:25-50. In some embodiments, the weight ratio of the organic stream to the aqueous stream in the settling tank is about 65:35. An additional amount of an aqueous liquid, an organic liquid, or both may be adding to the settling tank before, during, or after the one or more streams drawn from a process for co-producing propylene oxide and styrene monomer are disposed in the settling tank.

The aqueous stream of the settling tank, in some embodiments, includes (i) mono-propylene glycol, and (ii) a first amount of α-methyl benzyl alcohol, a first amount of benzaldehyde, a first amount of acetophenone, or a combination thereof. In some embodiments, the methods described herein include contacting the aqueous stream with an organic extraction liquid in a liquid-liquid extraction unit to form a first aqueous extraction stream and a first organic extraction stream; wherein the first aqueous extraction stream includes (i) mono-propylene glycol, and (ii) a second amount of α-methyl benzyl alcohol, a second amount of benzaldehyde, a second amount of acetophenone, or a combination thereof, and the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

In some embodiments, the second amount of α-methyl benzyl alcohol is about 20% to about 50%, about 25% to about 45%, or about 25% to about 35% less than the first amount of α-methyl benzyl alcohol. In other words, if the first amount is 100 units and the second amount is 25% less than the first amount, then the second amount is 75 units.

In some embodiments, the second amount of benzaldehyde is about 70% to about 99%, about 75% to about 99%, or about 80% to about 95% less than the first amount of benzaldehyde.

In some embodiments, the second amount of acetophenone is about 70% to about 99%, about 75% to about 99%, or about 80% to about 99% less than the first amount of acetophenone, respectively.

In some embodiments, the contacting of the aqueous stream with the organic extraction liquid includes mixing the aqueous stream and the organic extraction liquid. The aqueous stream and the organic extraction liquid may be mixed for about 5 seconds to about 60 seconds, about 5 seconds to about 30 seconds, or about 30 seconds. The mixing may be achieved by any known technique, such as stirring, moving (e.g., inverting) the liquid-liquid extraction unit, or a combination thereof. The methods also may include discontinuing mixing for a time sufficient to separate the aqueous stream and the organic extraction liquid. The time sufficient to separate the aqueous stream and the organic extraction liquid may be about 5 minutes to about 2 hours, about 30 minutes to about 1.5 hours, or about 1 hour.

The aqueous stream and the organic extraction liquid may be present at any weight ratio in the liquid-liquid extraction unit. In some embodiments, the aqueous stream and the organic extraction liquid are present in the liquid-liquid extraction unit at a weight ratio of about 0.5:1 to about 1:0.5, about 0.6:1 to about 1:0.6, about 0.7:1 to about 1:0.7, about 0.8:1 to about 1:0.8, about 0.9:1 to about 1:0.9, or about 1:1 (aqueous stream:organic extraction liquid).

The liquid-liquid extraction unit may be operated at any temperature and/or pressure that does not undesirably impact the methods described herein. In some embodiments, the pressure in the liquid extraction unit is ambient pressure. A pressure greater than ambient pressure may be used, however, in some embodiments. For example, the pressure in the liquid-liquid extraction unit may be about 1.1 bar to about 2 bar. In some embodiments, the temperature in the liquid-liquid extraction unit is about 20° C. to about 30° C. The phrase "the temperature in the liquid-liquid extraction unit" may refer to a temperature in the liquid-liquid extraction unit and/or the temperature of the contents of the liquid-liquid extraction unit. In some embodiments, an increased temperature may be used. For example, the contents of the liquid-liquid extraction unit may be heated before, during, and/or after the contents are disposed in the liquid-liquid extraction unit. For example, the temperature in the liquid-liquid extraction unit may be about 35° C. to about 75° C.

The liquid-liquid extraction unit may include known apparatus in which an extraction may be performed. In some embodiments, the liquid-liquid extraction unit includes a mixing-separating vessel, a liquid-liquid extraction column, a mixer-coalescer device, or a combination thereof.

The organic extraction liquid may include any organic liquid that is substantially insoluble in water (i.e., a solubility of less than 0.1 g per 100 mL of water at 20° C.). In some embodiments, the organic extraction liquid is an organic non-polar liquid. In some embodiments, the organic extraction liquid is an aromatic liquid, including an aromatic non-polar liquid. In some embodiments, the organic extraction liquid includes ethyl benzene, n-octane, toluene, or a combination thereof.

FIG. 1 is a schematic of a system 100 that may be used to perform embodiments of the methods described herein. The system 100 includes a settling tank 110 and a liquid-liquid extraction unit 120. In the embodiment depicted at FIG. 1, three purge streams (101, 102, 103) from a POSM process are combined and then disposed in the settling tank 110. In the settling tank 110, the three purge streams (101, 102, 103) separate into an organic stream 111 and an aqueous stream 112. The organic stream 111, in some embodiments, is optionally (i) purified, (ii) recycled into the POSM process from which the three purge streams (101, 102, 103) are drawn, or (iii) purified and recycled into the POSM process from which the three purge streams (101, 102, 103) are drawn. The aqueous stream 112 and an organic extraction liquid 113 are disposed in the liquid-liquid extraction unit 120. The contacting and subsequent separation of the aqueous stream 112 and the organic extraction liquid 113 produces an organic extraction stream 121 and an aqueous extraction stream 122. The aqueous extraction stream 122 may be subjected to further purification, such as the purification steps described herein, and the organic extraction stream 121 may be subjected to further purification, recycled into the POSM process from which the three purge streams (101, 102, 103) are drawn, or a combination thereof. In some embodiments, the three purge streams (101, 102, 103) include Stream 1, Stream 2, and Stream 3 of Example 1.

In some embodiments, the methods described herein also include contacting the first aqueous extraction stream with an additional amount of the organic extraction liquid to form a second aqueous extraction stream and a second organic extraction stream; wherein the second aqueous extraction stream includes (i) mono-propylene glycol, and (ii) a third amount of α-methyl benzyl alcohol, a third amount of benzaldehyde, a third amount of acetophenone, or a combination thereof, and the third amount of α-methyl benzyl alcohol, the third amount of benzaldehyde, and the third amount of acetophenone are less than the second amount of α-methyl benzyl alcohol, the second amount of benzaldehyde, and the second amount of acetophenone, respectively. The additional amount of the organic extraction liquid may include a new portion of the organic extraction liquid, a recycled portion of the organic extraction liquid, or a combination thereof. As depicted, for example, at FIG. 2 and FIG. 3, the organic extraction liquid may be purified, and then recycled to a liquid-liquid extraction unit.

In some embodiments, the third amount of α-methyl benzyl alcohol is about 20% to about 50%, about 25% to about 45%, or about 25% to about 35% less than the second amount of α-methyl benzyl alcohol. In other words, if the second amount is 100 units and the third amount is 25% less than the second amount, then the third amount is 75 units.

In some embodiments, the third amount of benzaldehyde is about 70% to about 99%, about 75% to about 99%, or about 80% to about 95% less than the second amount of benzaldehyde.

In some embodiments, the third amount of acetophenone is about 70% to about 99%, about 75% to about 99%, or about 80% to about 99% less than the second amount of acetophenone, respectively.

In some embodiments, the methods described herein include disposing the first aqueous extraction stream in a coalescer. The coalescer may include any apparatus that is configured to facilitate and/or promote the coalescence of small particles and/or droplets of hydrocarbons into larger particles and/or droplets. The coalescer of the methods described herein may include a mechanical coalescer or an electrostatic coalescer.

In some embodiments, the methods described herein include contacting a first aqueous extraction stream with activated carbon. The activated carbon may be in the form of an activated carbon bed. The activated carbon may remove at least a portion of impurities from the aqueous extraction stream through one or more mechanisms, such as adsorption.

In some embodiments, the methods include disposing the first aqueous extraction stream in an apparatus, such as a drying column, that is configured to isolate mono-propylene glycol from the first aqueous extraction stream. The methods, therefore, may include separating mono-propylene glycol from the first aqueous extraction stream.

In some embodiments, the methods described herein also include distilling at least one of the organic stream or the first organic extraction stream. The distilling may include a single distilling step or two or more distilling steps. In some embodiments, the distilling of at least one of the organic stream or the first organic extraction stream includes separating at least one of the organic stream or the first organic extraction stream into (i) a first distilled stream including ethyl benzene, styrene, or a combination thereof, (ii) a second distilled stream including benzaldehyde, (iii) a third distilled stream including α-methyl benzyl alcohol, acetophenone, or a combination thereof, or (iv) a combination thereof.

In some embodiments, the methods also include (i) disposing the first distilled stream in a liquid-liquid extraction unit, (ii) recycling the first distilled stream to a process for co-producing propylene oxide and styrene monomer, or (iii) a combination thereof. In some embodiments, the methods also include recycling the third distilled stream to a process for co-producing propylene oxide and styrene monomer.

Figure 2:
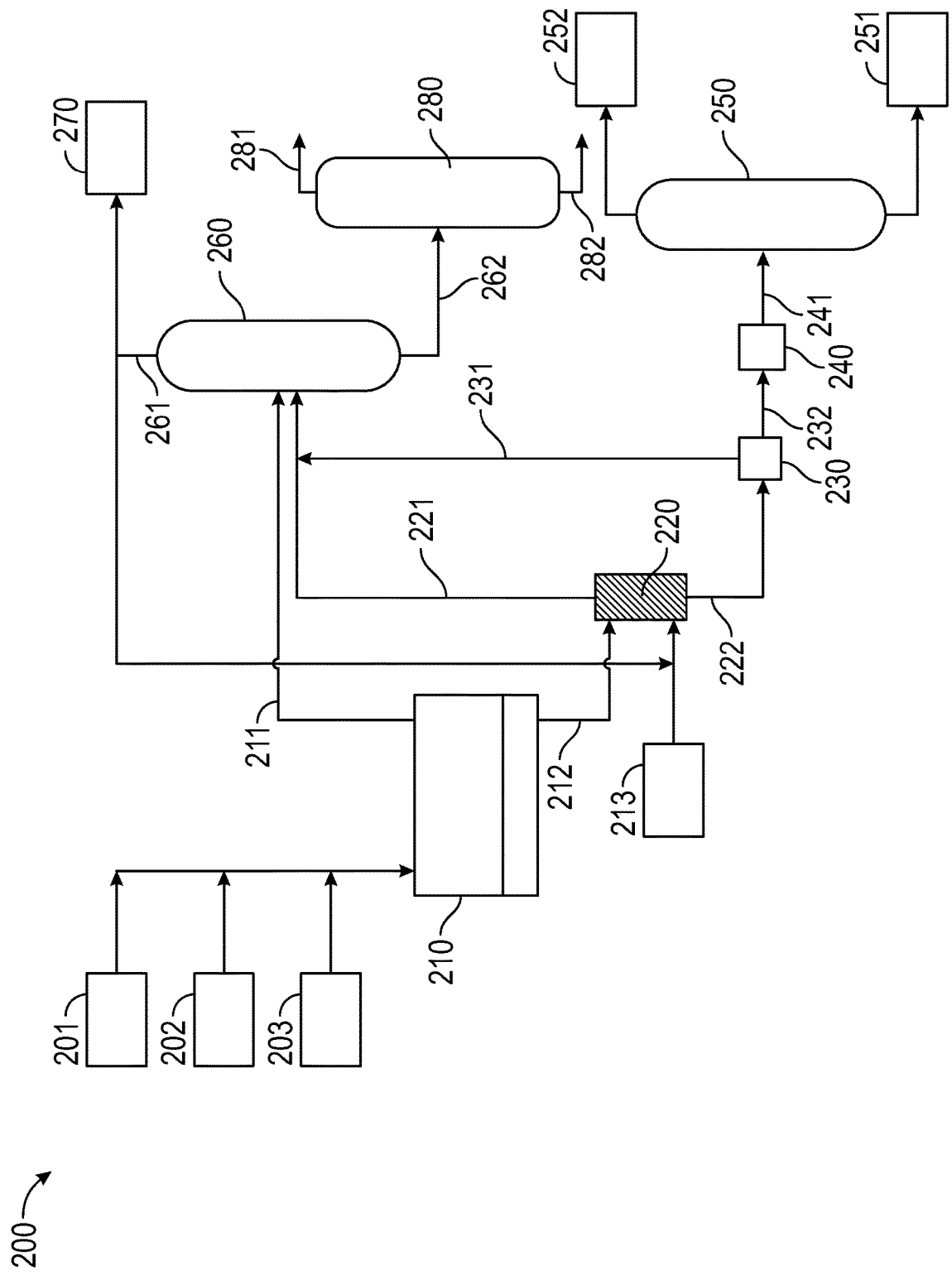
FIG. 2 depicts a schematic of an embodiment of a system for performing embodiments of the methods described herein.

FIG. 2 is a schematic of a system 200 that may be used to perform embodiments of the methods described herein. The system 200 includes a settling tank 210 and a liquid-liquid extraction unit 220. In the embodiment depicted at FIG. 2, three purge streams (201, 202, 203) from a POSM process are combined and then disposed in the settling tank 210. In the settling tank 210, the three purge streams (201, 202, 203) separate into an organic stream 211 and an aqueous stream 212. The weight ratio of the organic stream 211 to the aqueous stream 212 in the settling tank may be about 50-70:30-50; for example, about 65:35. The three purge streams (201, 202, 203), in some embodiments, are Stream 1, Stream 2, and Stream 3, respectively, of Example 1. The aqueous stream 212 and an organic extraction liquid 213 are disposed in the liquid-liquid extraction unit 220. The contacting and subsequent separation of the aqueous stream 212 and the organic extraction liquid 213 produces an organic extraction stream 221 and an aqueous extraction stream 222. The aqueous extraction stream 222 is then forwarded to a coalescer 230, which removes organic material 231 from the aqueous extraction stream 222 to produce a coalesced aqueous extraction stream 232, which is contacted with an activated carbon bed 240 to produce a cleaned coalesced aqueous extraction stream 241, which is disposed in a drying column 250 to isolate mono-propylene glycol 251 from water 252. The organic stream 211 from the settling tank 210, the organic extraction stream 221 from the liquid-liquid extraction unit 220, and the organic material 231 from the coalescer 230 are disposed in a column 260 that separates a light phase 261 (that includes the organic extraction liquid 213 and styrene) from a heavy phase 262 (that includes benzaldehyde, α-methyl benzyl alcohol, and acetophenone). The light phase 261 may be recycled by disposing the light phase 261 in the liquid-liquid extraction unit 220. The light phase 261 may be disposed directly in the liquid-liquid extraction unit 220, or combined, as shown, with the organic extraction liquid 213 prior to being disposed in the liquid-liquid extraction unit 220. The light phase 261 may be recycled into the POSM process 270 from which the three purge streams (201, 202, 203) are drawn. In some embodiments, the light phase 261 is recycled [1] to the liquid-liquid extraction unit 220 only, [2] to the POSM process 270 only, or [3] to both the liquid-liquid extraction unit 220 and the POSM process 270. The heavy phase 262 may be disposed into a column 280 to separate a stream including benzaldehyde 281 from a stream including α-methyl benzyl alcohol/acetophenone 282. The stream including α-methyl benzyl alcohol/acetophenone 282 may be used as fuel and/or recycled to the POSM process from which the three purge streams (201, 202, 203) are drawn.

Figure 3:
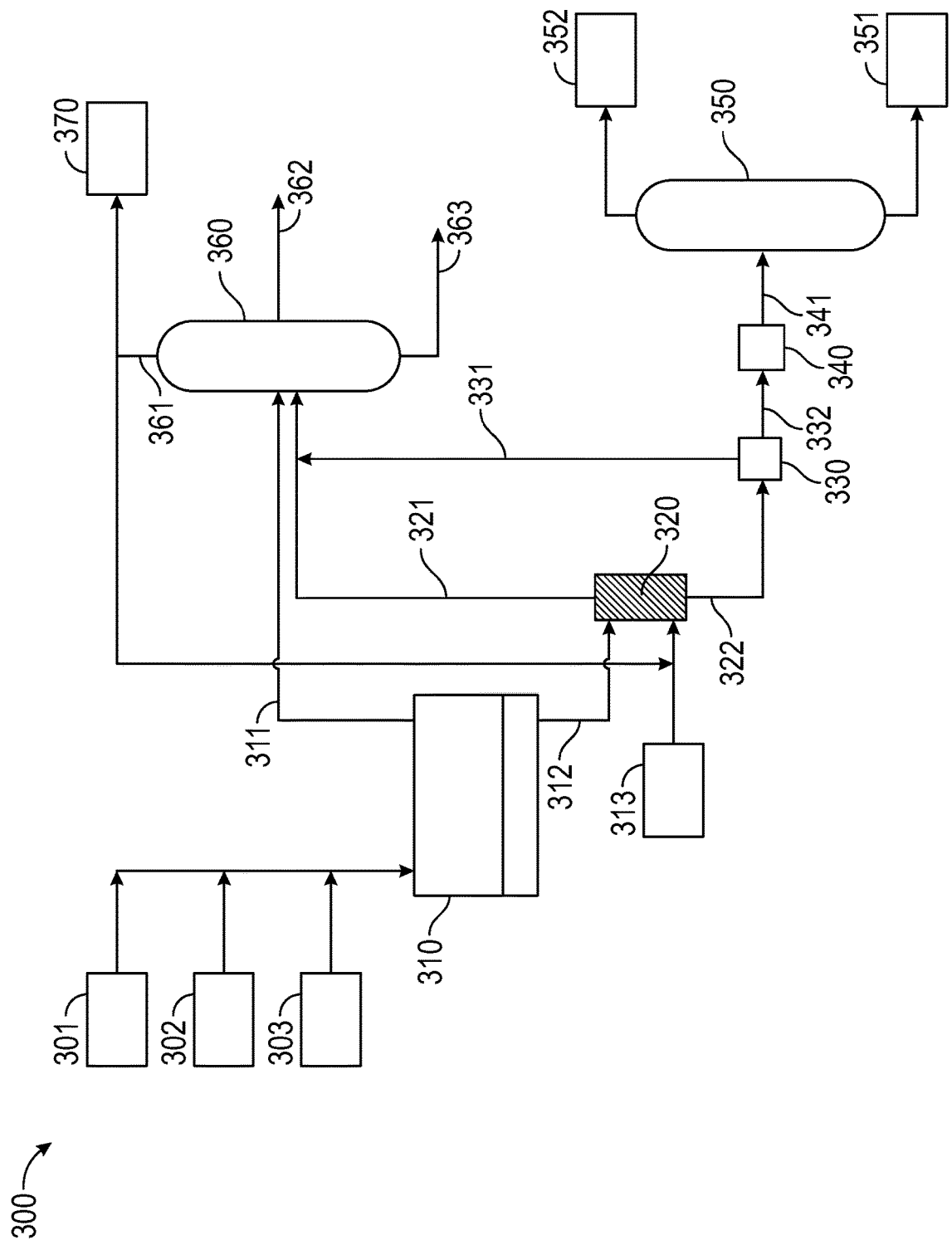
FIG. 3 depicts a schematic of an embodiment of a system for performing embodiments of the methods described herein.

FIG. 3 is a schematic of a system 300 that may be used to perform embodiments of the methods described herein. The system 300 includes a settling tank 310 and a liquid-liquid extraction unit 320. In the embodiment depicted at FIG. 3, three purge streams (301, 302, 303) from a POSM process are combined and then disposed in the settling tank 310. Alternatively, the three purge streams (301, 302, 303) may be directly disposed in the settling tank 310. In the settling tank 310, the three purge streams (301, 302, 303) separate into an organic stream 311 and an aqueous stream 312. The weight ratio of the organic stream 311 to the aqueous stream 312 in the settling tank may be about 50-70:30-50; for example, about 65:35. The three purge streams (301, 302, 303), in some embodiments, are Stream 1, Stream 2, and Stream 3, respectively, of Example 1. The aqueous stream 312 and an organic extraction liquid 313 are disposed in the liquid-liquid extraction unit 320. The contacting and subsequent separation of the aqueous stream 312 and the organic extraction liquid 313 produces an organic extraction stream 321 and an aqueous extraction stream 322. The aqueous extraction stream 322 is then forwarded to a coalescer 330, which removes organic material 331 from the aqueous extraction stream 322 to produce a coalesced aqueous extraction stream 332, which is contacted with an activated carbon bed 340 to produce a cleaned coalesced aqueous extraction stream 341, which is disposed in a drying column 350 to isolate mono-propylene glycol 351 from water 352. The organic stream 311 from the settling tank 310, the organic extraction stream 321 from the liquid-liquid extraction unit 320, and the organic material 331 from the coalescer 330 are disposed in a column 360 that separates the combined streams into a first stream 361 (that includes the organic extraction 313 and styrene), a second stream 362 that includes benzaldehyde, and a third stream 363 that includes α-methyl benzyl alcohol, and acetophenone. The first stream 361 may be recycled by disposing the first stream 361 in the liquid-liquid extraction unit 320. The first stream 361 may be disposed directly in the liquid-liquid extraction unit 320, or combined, as shown, with the organic extraction liquid 313 prior to being disposed in the liquid-liquid extraction unit 320. The first stream 361 may be recycled into the POSM process 370 from which the three purge streams (301, 302, 303) are drawn. In some embodiments, the first stream 361 is recycled [1] to the liquid-liquid extraction unit 320 only, [2] to the POSM process 370 only, or [3] to both the liquid-liquid extraction unit 320 and the POSM process 370. The third stream 363 including α-methyl benzyl alcohol/acetophenone may be used as fuel and/or recycled to the POSM process from which the three purge streams (301, 302, 303) are drawn.

Figure 4:
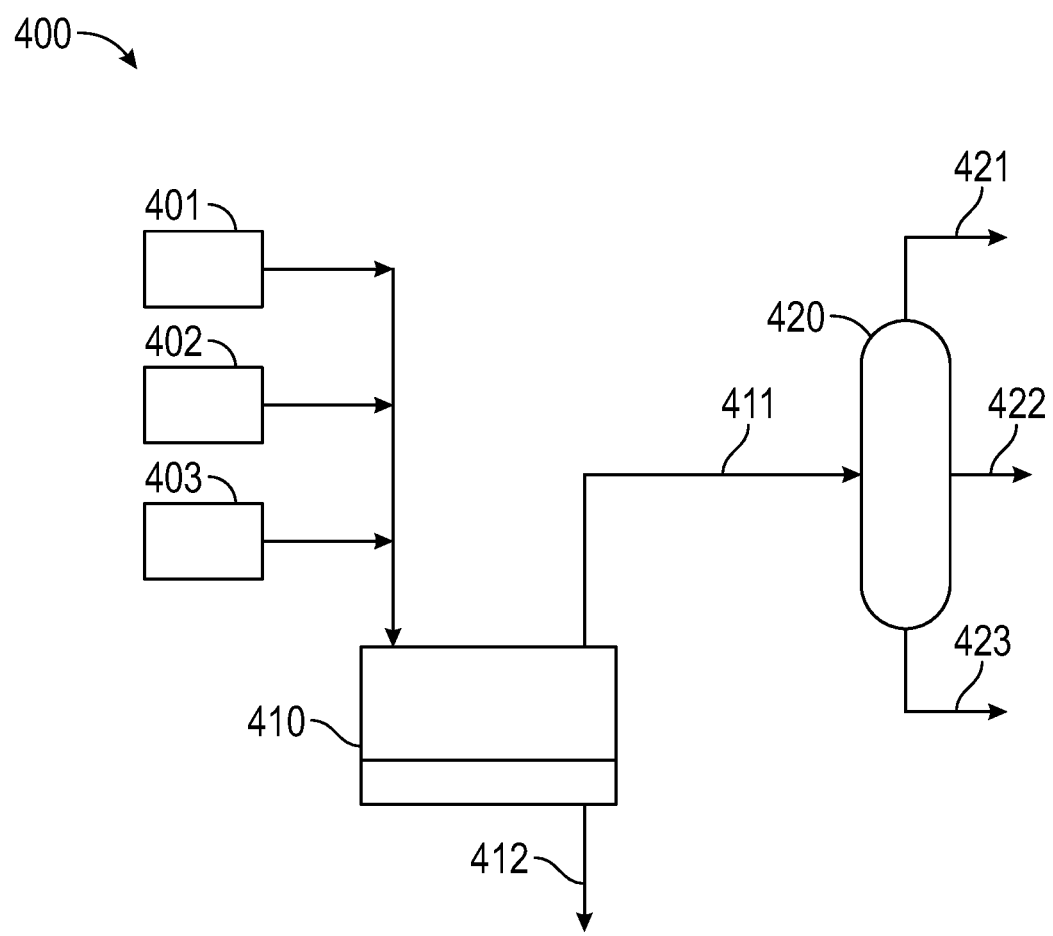
FIG. 4 depicts a schematic of an embodiment of a system for performing embodiments of the methods described herein.

FIG. 4 is a schematic of a system 400 that may be used to perform embodiments of the methods described herein. The system 400 includes a settling tank 410 and a column 420. In the embodiment depicted at FIG. 4, three purge streams (401, 402, 403) from a POSM process are combined and then disposed in the settling tank 410. Alternatively, the three purge streams (401, 402, 403) may be directly disposed in the settling tank 410. In the settling tank 410, the three purge streams (401, 402, 403) separate into an organic stream 411 and an aqueous stream 412. The weight ratio of the organic stream 411 to the aqueous stream 412 in the settling tank 410 may be about 50-70:30-50; for example, about 65:35. The three purge streams (401, 402, 403), in some embodiments, are Stream 1, Stream 2, and Stream 3, respectively, of Example 1. The aqueous stream 412 may be contacted with an organic extraction liquid as described herein. The organic stream 411 from the settling tank 410 is disposed in a column 420 that separates the stream into a first stream 421 that includes styrene, a second stream 422 that includes benzaldehyde, and a third stream 423 that includes α-methyl benzyl alcohol and acetophenone. The first stream 421 may be recycled into a POSM process from which the three purge streams (401, 402, 403) are drawn. The third stream 423 including α-methyl benzyl alcohol/acetophenone may be used as fuel and/or recycled to a POSM process from which the three purge streams (401, 402, 403) are drawn.

Figure 5:
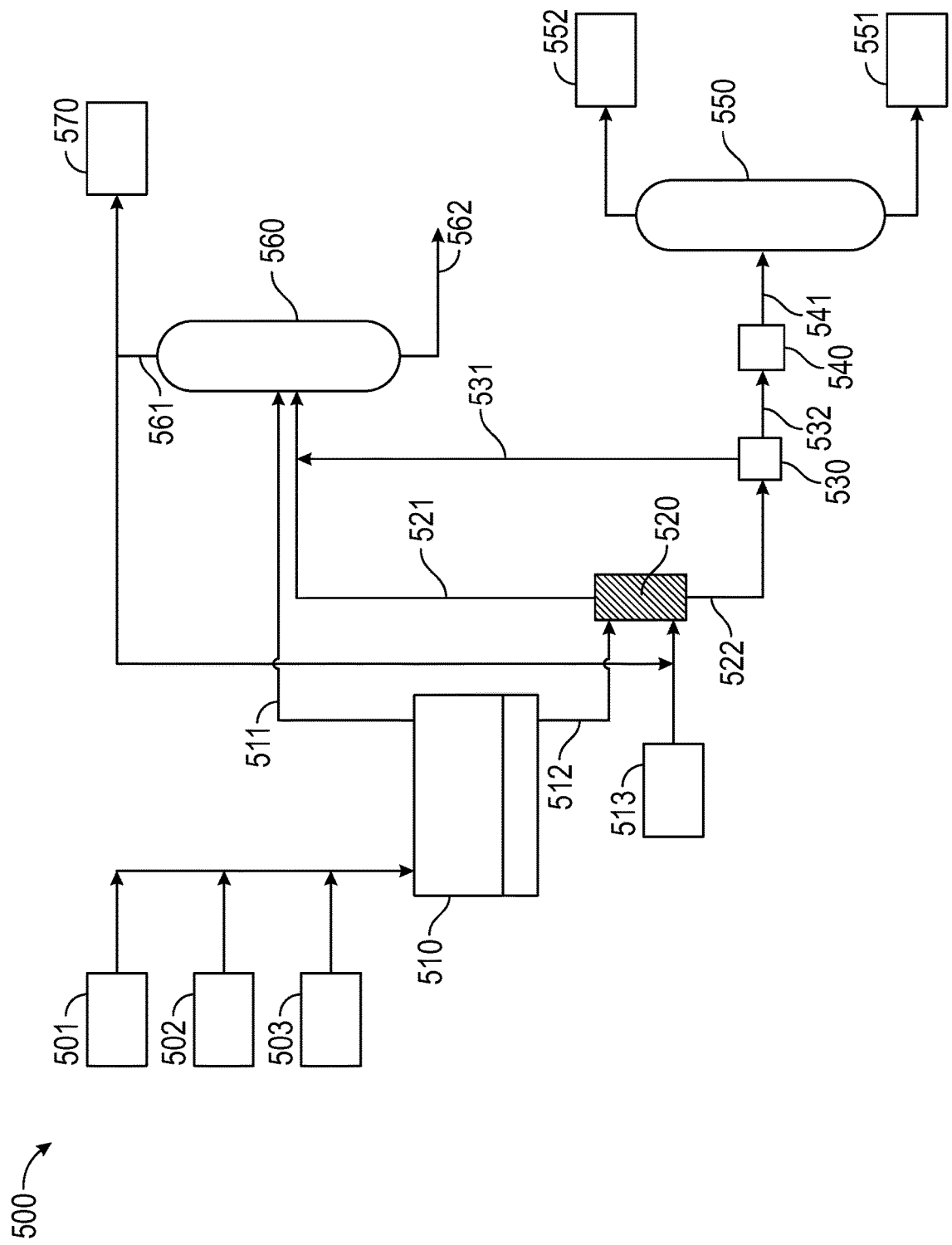
FIG. 5 depicts a schematic of an embodiment of a system for performing embodiments of the methods described herein.

FIG. 5 is a schematic of a system 500 that may be used to perform embodiments of the methods described herein. The system 500 includes a settling tank 510 and a liquid-liquid extraction unit 520. The liquid-liquid extraction unit 520 may be a counter current liquid-liquid extraction unit having a packed-bed style. In the embodiment depicted at FIG. 5, three purge streams (501, 502, 503) from a POSM process are combined and then disposed in the settling tank 510. Alternatively, the three purge streams (501, 502, 503) may be directly disposed in the settling tank 510. In the settling tank 510, the three purge streams (501, 502, 503) separate into an organic stream 511 and an aqueous stream 512. The weight ratio of the organic stream 511 to the aqueous stream 512 in the settling tank may be about 50-70:30-50; for example, about 65:35. The three purge streams (501, 502, 503), in some embodiments, are Stream 1, Stream 2, and Stream 3, respectively, of Example 1. The aqueous stream 512 and an organic extraction liquid 513 are disposed in the liquid-liquid extraction unit 520. The contacting and subsequent separation of the aqueous stream 512 and the organic extraction liquid 513 produces an organic extraction stream 521 and an aqueous extraction stream 522. The aqueous extraction stream 522 is then forwarded to a coalescer 530, which removes organic material 531 from the aqueous extraction stream 522 to produce a coalesced aqueous extraction stream 532, which is contacted with an activated carbon bed 540 to produce a cleaned coalesced aqueous extraction stream 541, which is disposed in a drying column 550 to isolate mono-propylene glycol 551 from water 552. The organic stream 511 from the settling tank 510, the organic extraction stream 521 from the liquid-liquid extraction unit 520, and the organic material 531 from the coalescer 530 are disposed in a column 560 that separates the combined streams into a first stream 561 (that includes the organic extraction 513 and styrene), a second stream 562 that includes "heavies" or "bottom organics" (e.g., benzaldehyde, α-methyl benzyl alcohol, acetophenone, or a combination thereof). The first stream 561 may be recycled by disposing the first stream 561 in the liquid-liquid extraction unit 520. The first stream 561 may be disposed directly in the liquid-liquid extraction unit 520, or combined, as shown, with the organic extraction liquid 513 prior to being disposed in the liquid-liquid extraction unit 520. The first stream 561 may be recycled into the POSM process 570 from which the three purge streams (501, 502, 503) are drawn. In some embodiments, the first stream 561 is recycled [1] to the liquid-liquid extraction unit 520 only, [2] to the POSM process 570 only, or [3] to both the liquid-liquid extraction unit 520 and the POSM process 570. The second stream 562 may be used as fuel and/or recycled to the POSM process from which the three purge streams (501, 502, 503) are drawn.

In some embodiments, the methods also include separating mono-propylene glycol, benzaldehyde, α-methyl benzyl alcohol, acetophenone, or a combination thereof from the first aqueous extraction stream, a first organic extraction stream, or a combination thereof. The separation may be achieved using any one or more known apparatuses or methods, or apparatuses or methods described herein.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

In the descriptions provided herein, the terms "includes," "is," "containing," "having," and "comprises" are used in an open-ended fashion, and thus should be interpreted to mean "including, but not limited to." When methods and systems are claimed or described in terms of "comprising" various components or steps, the systems and methods can also "consist essentially of" or "consist of" the various components or steps, unless stated otherwise.

The terms "a," "an," and "the" are intended to include plural alternatives, e.g., at least one. For instance, the disclosure of "a stream," "an organic extraction liquid," "a settling tank", and the like, are meant to encompass one, or mixtures or combinations of more than one stream, organic extraction liquid, settling tank, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, a temperature in a liquid-liquid extraction unit is "about 20° C. to about 30° C.". This range should be interpreted as encompassing temperatures of about 20° C. and about 30° C., and further encompasses "about" each of 21° C., 22° C., 23° C., 24° C., 25° C., 26° C., 27° C., 28° C., and 29° C., including any ranges and sub-ranges between any of these values.

The term "about", as used herein, refers to values that are within 5% of the indicated value. For example, "about 20° C." would encompass pressures of 19° C. to 21° C.

EXAMPLES

The present disclosure is further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects of this disclosure will be apparent to those skilled in the art from consideration of the specification and practice of the disclosure disclosed herein.

Example 1

Analysis of POSM Purge Streams

In this example, three purge streams from a POSM processes were collected and analyzed. The streams are arbitrarily labeled "1", "2", and "3" in the following tables, which also provide the average weight percentages of the components of the streams.

TABLE 1

Analysis of Stream 1

| Component | Stream 1 Average (wt. %) |
|---|---|
| Water | 8.5 |
| Ethyl-benzene | 0.2 |
| Benzaldehyde | 11.5 |
| Mono-Propylene Glycol | 68.6 |
| Acetophenone | 5.4 |
| α-Methyl Benzyl Alcohol | 0.7 |
| Others | 5.1 |

TABLE 2

Analysis of Stream 2

| Component | Stream 2 Average (wt. %) |
|---|---|
| Water | 11.1 |
| Ethyl-benzene | 0.6 |
| Benzaldehyde | 26.0 |
| Mono-Propylene Glycol | 45.5 |
| Acetophenone | 4.7 |
| α-Methyl Benzyl Alcohol | 0.8 |
| Others | 11.3 |

The foregoing table provides the average weight percentages of each component of Stream 2.

TABLE 3

Analysis of Stream 3

| Component | Stream 3 Average (wt. %) |
|---|---|
| Water | 81.31 |
| Mono-propylene glycol | 17.81 |
| Other Organics | 0.88 |

Although one or more of the streams of this example were subjected to the processes described in the following examples, other streams from POSM processes may be subjected to the methods described herein, including those of the following examples.

Example 2

Extraction with Ethyl Benzene

In this example, a liquid-liquid extraction was performed with ethyl benzene on an aqueous stream separated from Sample A of Stream 1. Sample A, prior to extraction, was subjected to GC-FID analysis, which revealed three significant peaks that corresponded to mono-propylene glycol, benzaldehyde, and α-methyl benzyl alcohol/acetophenone.

A 1:1 weight ratio of [1] ethyl benzene and [2] the aqueous stream separated from Sample A of Stream 1 were disposed in a liquid-liquid extraction unit at ambient temperature and ambient pressure. The contents of the extraction unit were mixed for 15 seconds, and allowed to separate for 1 hour.

The liquid-liquid extraction unit included an organic stream and an aqueous stream, which were subjected to GC-FID analysis. The analysis of the aqueous stream after the extraction with ethyl benzene revealed three peaks, the first corresponding to mono-propylene glycol, the second corresponding to ethyl benzene, and the third corresponding to α-methyl benzyl alcohol and acetophenone. The benzaldehyde peak, which appeared in the GC-FID analysis prior to extraction, was no longer present. Also observed was a reduction of α-methyl benzyl alcohol and acetophenone, compared to the GC-FID analysis conducted prior to the extraction. The ethylene benzene was then removed.

The GC-FID analysis of the organic stream of this example after the extraction revealed three peaks, the first corresponding to ethyl benzene, the second corresponding to benzaldehyde, and the third corresponding to α-methyl benzyl alcohol and acetophenone.

The extraction efficiency for the three consecutive passes of this example are provided in the following table.

TABLE 4

Liquid-Liquid Extraction Efficiency with Ethyl Benzene

| Component | Percentage Total Reduction in Aqueous Stream | | |
|---|---|---|---|
| | Pass 1 | Pass 2 | Pass 3 |
| Benzaldehyde | 94.9 | 99.7 | 99.8 |
| α-Methyl Benzyl Alcohol | 65.8 | 83.7 | 92.9 |
| Acetophenone | 93.2 | 98.9 | 99.4 |

The foregoing table provides the average weight percentages of each component of Stream 3.

Although a sample of Stream 1 was used in this example, the procedure of this example may be applied to other streams, including, but not limited to, Stream 2, Stream 3, and/or other streams, including purge streams, from a POSM process; or the procedure may be applied to a combination of streams, including, but not limited to, a combination that includes at least two of Stream 1, Stream 2, Stream 3, another stream from a POSM process, or a combination thereof.

Although the contents of the liquid-liquid extraction unit of this example were subjected to ambient temperature and ambient pressure, other temperatures and/or pressures may be used.

Example 3

Extraction with n-Octane

In this example, a liquid-liquid extraction was performed with n-octane on an aqueous stream separated from Sample A of Stream 1. As in Example 2, Sample A, prior to extraction, was subjected to GC-FID analysis, which revealed three significant peaks that corresponded to monopropylene glycol, benzaldehyde, and α-methyl benzyl alcohol/acetophenone.

A 1:1 weight ratio of [1] n-octane and [2] the aqueous stream separated from Sample A of Stream 1 were disposed in a liquid-liquid extraction unit at ambient temperature and ambient pressure. The contents of the extraction unit were mixed for 15 seconds, and allowed to settle for 1 hour.

After separating, the liquid-liquid extraction unit included an organic stream and an aqueous stream, which were subjected to GC-FID analysis in order to determine the extraction efficiency. After three passes, the GC-FID data indicated a very low concentration of mono propylene glycol in the organic stream.

The extraction efficiency for the three consecutive passes of this example are provided in the following table.

TABLE 5

Liquid-Liquid Extraction Efficiency with n-Octane

| Component | Percentage Total Reduction in Aqueous Stream | | |
|---|---|---|---|
| | Pass 1 | Pass 2 | Pass 3 |
| Benzaldehyde | 78.0 | 93.6 | 98.3 |
| α-Methyl Benzyl Alcohol | 29.0 | 34.8 | 47.2 |
| Acetophenone | 73.9 | 90.9 | 96.7 |

The results of this example were indicative of the very low solubility of n-octane in the aqueous stream that included water and mono propylene glycol. This feature of n-octane reduced the complexity of the glycol purification process of this example. Also, due to the fact that mono propylene glycol has a very low solubility in n-octane, the loss of mono propylene glycol in the organic stream was reduced or minimized in this example.

The n-octane of this example was purified and recycled via distillation, which was a relatively simple process due at least in part to the fact that n-octane has a much lower boiling point than most, if not all, of the other components of the organic stream. Moreover, n-octane is already used in many POSM processes, which can provide an option for integration.

Although a sample of Stream 1 was used in this example, the procedure of this example may be applied to other streams, including, but not limited to, Stream 2, Stream 3, and/or other streams, including purge streams, from a POSM process; or the procedure may be applied to a combination of streams, including, but not limited to, a combination that includes at least two of Stream 1, Stream 2, Stream 3, another stream from a POSM process, or a combination thereof.

Although the contents of the liquid-liquid extraction unit of this example were subjected to ambient temperature and ambient pressure, other temperatures and/or pressures may be used.

Example 4

Extraction with Toluene

In this example, a liquid-liquid extraction was performed with toluene on an aqueous stream separated from Sample A of Stream 1. As in Examples 2 and 3, Sample A, prior to extraction, was subjected to GC-FID analysis, which revealed three significant peaks that corresponded to monopropylene glycol, benzaldehyde, and α-methyl benzyl alcohol/acetophenone.

A 1:1 weight ratio of [1] toluene and [2] the aqueous stream separated from Sample A of Stream 1 were disposed in a liquid-liquid extraction unit at ambient temperature and ambient pressure. The contents of the extraction unit were mixed for 15 seconds, and allowed to settle for 1 hour.

After separating, the liquid-liquid extraction unit included an organic stream and an aqueous stream, which were subjected to GC-FID analysis in order to determine the extraction efficiency.

The extraction efficiency for the three consecutive passes of this example are provided in the following table.

TABLE 6

Liquid-Liquid Extraction Efficiency with Toluene

| Component | Percentage Total Reduction in Aqueous Stream | | |
|---|---|---|---|
| | Pass 1 | Pass 2 | Pass 3 |
| Benzaldehyde | 77.7 | 99.8 | 100 |
| α-Methyl Benzyl Alcohol | 69.3 | 89.0 | 95.5 |
| Acetophenone | 89.2 | 99.8 | 100 |

The results of this example were indicative of the very low solubility of toluene in the aqueous stream that included water and mono propylene glycol. This feature of toluene reduced the complexity of the glycol purification process of this example. Also, due to the fact that mono propylene glycol has a very low solubility in toluene, the loss of mono propylene glycol in the organic stream was reduced or minimized in this example.

The toluene of this example was purified and recycled via distillation, which was a relatively simple process due at least in part to the fact that toluene has a much lower boiling point than most, if not all, of the other components of the organic stream. Moreover, toluene is already used in many POSM processes, which can provide an option for integration.

Although a sample of Stream 1 was used in this example, the procedure of this example may be applied to other streams, including, but not limited to, Stream 2, Stream 3, and/or other streams, including purge streams, from a POSM process; or the procedure may be applied to a combination of streams, including, but not limited to, a combination that includes at least two of Stream 1, Stream 2, Stream 3, another stream from a POSM process, or a combination thereof.

Although the contents of the liquid-liquid extraction unit of this example were subjected to ambient temperature and ambient pressure, other temperatures and/or pressures may be used.

Example 5

Vacuum Distillation

This example illustrates how the organic layer is separated into three fractions using a vacuum distillation column. A 20 tray 1 inch internal diameter Oldershaw glass vacuum column was used for this experiment. The batch distillation was conducted at approximately 20 mmHg. Different vacuum pressures can be used, however, distillation at pressures higher than 20 mmHg will lead to higher bottom temperatures, thus, higher energy usage. From a 200 gr organic phase containing 34% benzaldehyde, via vacuum distillation, three fractions were collected as in the following Table 7.

TABLE 7

Composition of Distillation Cuts

| Fractions | Mass (gr) | Mass percent of feed | Main components |
|---|---|---|---|
| Light fraction | 37 | 18% | Light components including ethyl benzene and styrene |
| Middle fraction | 88 | 44% | Benzaldehyde at approximately 60 wt % and other heavies impurities. Majority of benzaldehyde was recovered in this fraction. |
| Heavies fraction (reboiler) | 75 | 38% | MBA, ACP and other heavies components. |

Example 6

Aqueous Phase Extraction

This example illustrates how the aqueous phase is extracted with ethylbenzene to reduce the organic content, and then water is removed from the mixture using vacuum distillation. Table 8 provides the composition of the aqueous phase before being processed.

TABLE 8

Composition of Aqueous Phase

| Component | Mass Fraction (wt. %) |
|---|---|
| MPG | 38.2 |
| Water | 19.0 |
| Other heavier organic chemicals | 42.8 |

A single liquid-liquid extraction on the above aqueous phase with ethyl benzene (1:1 ratio) at ambient temperature and atmospheric pressure. The water in the resulting aqueous extraction stream was then reduced using a 20 tray, 1 inch internal diameter Oldershaw glass vacuum distillation column at 25 mmHg. The composition of the bottom product is provided in Table 9.

TABLE 9

Composition of Treated MPG Stream

| Component | Mass Fraction (wt. %) |
|---|---|
| MPG | 82.3 |
| Water | 2.7 |
| Other heavier organic chemicals | 15 |

We claim:

1. A method for recovering one or more chemicals, the method comprising:
   providing at least one stream from a process for co-producing propylene oxide and styrene monomer;
   disposing the at least one stream in a settling tank to separate the at least one stream into an aqueous stream and an organic stream, wherein the aqueous stream comprises (i) mono-propylene glycol, and (ii) a first amount of α-methyl benzyl alcohol, a first amount of benzaldehyde, a first amount of acetophenone, or a combination thereof;
   contacting the aqueous stream with an organic extraction liquid in a liquid-liquid extraction unit to form a first aqueous extraction stream and a first organic extraction stream; and
   disposing the first aqueous extraction stream in a coalescer;
   wherein the first aqueous extraction stream comprises (i) mono-propylene glycol, and (ii) a second amount of α-methyl benzyl alcohol, a second amount of benzaldehyde, a second amount of acetophenone, or a combination thereof; and wherein the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

2. The method of claim 1, further comprising contacting the first aqueous extraction stream with an additional amount of the organic extraction liquid to form a second aqueous extraction stream and a second organic extraction stream; wherein the second aqueous extraction stream comprises (i) mono-propylene glycol, and (ii) a third amount of α-methyl benzyl alcohol, a third amount of benzaldehyde, a third amount of acetophenone, or a combination thereof, and the third amount of α-methyl benzyl alcohol, the third amount of benzaldehyde, and the third amount of acetophenone are less than the second amount of α-methyl benzyl alcohol, the second amount of benzaldehyde, and the second amount of acetophenone, respectively.

3. The method of claim 1, further comprising contacting the first aqueous extraction stream with activated carbon.

4. The method of claim 1, further comprising disposing the first aqueous extraction stream in an apparatus configured to isolate mono-propylene glycol from the first aqueous extraction stream.

5. The method of claim 1, wherein the aqueous stream and the organic extraction liquid are present in the liquid-liquid extraction unit at a weight ratio of about 0.5:1 to about 1:0.5 (aqueous stream:organic extraction liquid).

6. The method of claim 1, further comprising distilling at least one of the organic stream or the first organic extraction stream.

7. The method of claim 6, wherein the distilling of at least one of the organic stream or the first organic extraction stream comprises separating from at least one of the organic stream or the first organic extraction stream (i) a first distilled stream comprising ethyl benzene, styrene, or a combination thereof, (ii) a second distilled stream comprising benzaldehyde, (iii) a third distilled stream comprising α-methyl benzyl alcohol, acetophenone, or a combination thereof, or (iv) a combination thereof.

8. The method of claim 7, further comprising (i) disposing the first distilled stream in the liquid-liquid extraction unit, (ii) recycling the first distilled stream to the process for co-producing propylene oxide and styrene monomer, or (iii) a combination thereof.

9. The method of claim 7, further comprising recycling the third distilled stream to the process for co-producing propylene oxide and styrene monomer.

10. The method of claim 1, wherein the liquid-liquid extraction unit comprises a mixing-separating vessel, a liquid-liquid extraction column, a mixer-coalescer device, or a combination thereof.

11. The method of claim 1, wherein the organic extraction liquid comprises ethyl benzene, n-octane, toluene, or a combination thereof.

12. The method of claim 1, further comprising separating mono-propylene glycol, benzaldehyde, α-methyl benzyl alcohol, acetophenone, or a combination thereof from the first aqueous extraction stream, the first organic extraction stream, or a combination thereof.

13. A method for recovering one or more chemicals, the method comprising:

providing at least one stream from a process for co-producing propylene oxide and styrene monomer;

disposing the at least one stream in a settling tank to separate the at least one stream into an aqueous stream and an organic stream, wherein the aqueous stream comprises (i) mono-propylene glycol, and (ii) a first amount of α-methyl benzyl alcohol, a first amount of benzaldehyde, a first amount of acetophenone, or a combination thereof; and contacting the aqueous stream with an organic extraction liquid in a liquid-liquid extraction unit to form a first aqueous extraction stream and a first organic extraction stream; and contacting the first aqueous extraction stream with activated carbon;

wherein the first aqueous extraction stream comprises (i) mono-propylene glycol, and (ii) a second amount of α-methyl benzyl alcohol, a second amount of benzaldehyde, a second amount of acetophenone, or a combination thereof; and wherein the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

14. The method of claim 13, wherein the aqueous stream and the organic extraction liquid are present in the liquid-liquid extraction unit at a weight ratio of about 0.5:1 to about 1:0.5 (aqueous stream:organic extraction liquid).

15. The method of claim 13, further comprising distilling at least one of the organic stream or the first organic extraction stream.

16. The method of claim 15, wherein the distilling of at least one of the organic stream or the first organic extraction stream comprises separating from at least one of the organic stream or the first organic extraction stream (i) a first distilled stream comprising ethyl benzene, styrene, or a combination thereof, (ii) a second distilled stream comprising benzaldehyde, (iii) a third distilled stream comprising α-methyl benzyl alcohol, acetophenone, or a combination thereof, or (iv) a combination thereof.

17. The method of claim 16, further comprising (i) disposing the first distilled stream in the liquid-liquid extraction unit, (ii) recycling the first distilled stream to the process for co-producing propylene oxide and styrene monomer, or (iii) a combination thereof.

18. A method for recovering one or more chemicals, the method comprising:

providing at least one stream from a process for co-producing propylene oxide and styrene monomer;

disposing the at least one stream in a settling tank to separate the at least one stream into an aqueous stream and an organic stream, wherein the aqueous stream comprises (i) mono-propylene glycol, and (ii) a first amount of α-methyl benzyl alcohol, a first amount of benzaldehyde, a first amount of acetophenone, or a combination thereof; and contacting the aqueous stream with an organic extraction liquid in a liquid-liquid extraction unit to form a first aqueous extraction stream and a first organic extraction stream; and disposing the first aqueous extraction stream in an apparatus configured to isolate mono-propylene glycol from the first aqueous extraction stream;

wherein the first aqueous extraction stream comprises (i) mono-propylene glycol, and (ii) a second amount of α-methyl benzyl alcohol, a second amount of benzaldehyde, a second amount of acetophenone, or a combination thereof; and wherein the second amount of α-methyl benzyl alcohol, the second amount of benzaldehyde, and the second amount of acetophenone are less than the first amount of α-methyl benzyl alcohol, the first amount of benzaldehyde, and the first amount of acetophenone, respectively.

19. The method of claim 18, wherein the aqueous stream and the organic extraction liquid are present in the liquid-liquid extraction unit at a weight ratio of about 0.5:1 to about 1:0.5 (aqueous stream:organic extraction liquid).

20. The method of claim 18, further comprising distilling at least one of the organic stream or the first organic extraction stream.

21. The method of claim 20, wherein the distilling of at least one of the organic stream or the first organic extraction stream comprises separating from at least one of the organic stream or the first organic extraction stream (i) a first distilled stream comprising ethyl benzene, styrene, or a combination thereof, (ii) a second distilled stream comprising benzaldehyde, (iii) a third distilled stream comprising α-methyl benzyl alcohol, acetophenone, or a combination thereof, or (iv) a combination thereof.

22. The method of claim 21, further comprising (i) disposing the first distilled stream in the liquid-liquid extraction unit, (ii) recycling the first distilled stream to the process for co-producing propylene oxide and styrene monomer, or (iii) a combination thereof.

* * * * *